United States Patent [19]
Hirano

[11] Patent Number: 6,090,349
[45] Date of Patent: Jul. 18, 2000

[54] DIFFUSER

[76] Inventor: Mutsuo Hirano, 10-3, Motobuto 5-chome, Urawa-shi, Saitama, 336-0004, Japan

[21] Appl. No.: 09/006,397

[22] Filed: Jan. 12, 1998

[30] Foreign Application Priority Data

Jan. 13, 1997 [JP] Japan ................................ 9-004041

[51] Int. Cl.$^7$ ...................................................... A61L 9/03
[52] U.S. Cl. ......................... 422/124; 422/125; 422/305; 392/393; 392/403
[58] Field of Search ................................ 422/124, 125, 422/4, 5, 305; 392/393, 394, 403

[56] References Cited

U.S. PATENT DOCUMENTS

| | | | |
|---|---|---|---|
| 2,468,164 | 4/1949 | Brewster | 422/125 X |
| 2,668,993 | 2/1954 | Bair | 422/125 |
| 3,080,624 | 3/1963 | Weber, III | 422/125 |
| 3,770,199 | 11/1973 | Hoek et al. | 239/54 |
| 3,923,458 | 12/1975 | Moran | 422/125 X |
| 3,948,445 | 4/1976 | Andeweg | 422/125 X |
| 3,973,493 | 8/1976 | Black et al. | 101/126 |
| 4,216,176 | 8/1980 | Tanaka | 261/142 |
| 4,627,963 | 12/1986 | Olson | 422/125 |
| 4,695,435 | 9/1987 | Spector | 422/124 |
| 4,808,347 | 2/1989 | Dawn | 422/124 X |
| 4,849,181 | 7/1989 | Kelley et al. | 422/125 X |
| 5,788,931 | 8/1998 | Quintana | 422/125 |

*Primary Examiner*—Elizabeth McKane
*Attorney, Agent, or Firm*—Lowe Hauptman Gopstein Gilman & Berner

[57] ABSTRACT

A diffuser is a structure having a porous diffusing member into which aromatic matter or the like is impregnated and an incandescent lamp accelerating diffusion of the aromatic matter or the like impregnated into the diffusing member. When using the diffuser liquid aromatic matter is dropped into the diffusing member, after which the incandescent lamp is actuated. The actuated incandescent lamp accelerates diffusion of the aromatic matter impregnated into the diffusing member, so that the aromatic matter may be diffused over the whole room in a short time.

5 Claims, 14 Drawing Sheets

DIFFUSER

BACKGROUND OF THE INVENTION

1. Field of the Invention

The present invention relates to a diffuser suitable for humidification, aromatization, deodorization or insecticide.

2. Description of the Prior Art

As said type of diffusers, for example diffusers for aromatizing the air in a room, an aromatic lamp or aromatic plate has been generally used.

The aromatic lamp uses an incandescent lamp as a heat source, to which liquid aromatic matter is dropped so as to be diffused over the room by heat generated from the lamp. The liquid aromatic matter used is essential oil distilled from plants, such as petals of roses, rind of lemons, etc. or its aqueous solution, known as aromatic oil.

The aromatic plate is a small plate with water into which said liquid aromatic matter is dropped, wherein the aromatic matter is diffused over the room by placing the plate on a heat source such as a stove to heat it.

However, in either case of the aromatic lamp or the aromatic plate, it has been a problem that, since most part of the aromatic matter is in contact with the surrounding air, dust and bacteria suspended in the air easily adhere to the aromatic matter, which makes the aromatic matter to be susceptible to deterioration.

Further, in the case of the aromatic lamp and the aromatic plate, since nothing but heating is done to diffuse the aromatic matter, diffusion of the aromatic matter is left to its course, which causes a problem that it takes a long time for the aromatic matter to be diffused over the whole room.

SUMMARY OF THE INVENTION

It is an object of the present invention to provide a diffuser capable of preventing aromatic matter from being deteriorated and capable of allowing the aromatic matter to be diffused over the whole room in a short time.

The feature of the diffuser made pursuant to the first present invention is that it has a container storing water, liquid aromatic matter, liquid deodorant matter or liquid insecticidal matter as well as a porous diffusing member into which the matter stored in the container is impregnated.

According to the first present invention, of the liquid matter impregnated into the diffusing member only some which exists on the surface of the diffusing member comes into contact with the surrounding air. Accordingly the deterioration of the aromatic matter or the like may be retarded.

The feature of the diffuser made pursuant to the second present invention is that it has a porous diffusing member into which water, liquid aromatic matter, liquid deodorant matter or liquid insecticidal matter is impregnated as well as a diffusion accelerator accelerating diffusion of the matter impregnated into the diffusing member.

According to the second present invention, when using the diffuser liquid aromatic matter or the like is dropped into the diffusing member, after which the diffusion accelerator is actuated. The actuated diffusion accelerator accelerates diffusion of the aromatic matter or the like impregnated into the diffusing member, so that the aromatic matter or the like may be diffused over the whole room in a short time.

The above and other objects, features and advantages of the present invention will be apparent from the following description and the accompanying drawings.

DESCRIPTION OF THE PREFERRED EMBODIMENTS

FIGS. 1–5 illustrate a diffuser made pursuant to the first embodiment of the present invention.

Figure 2:
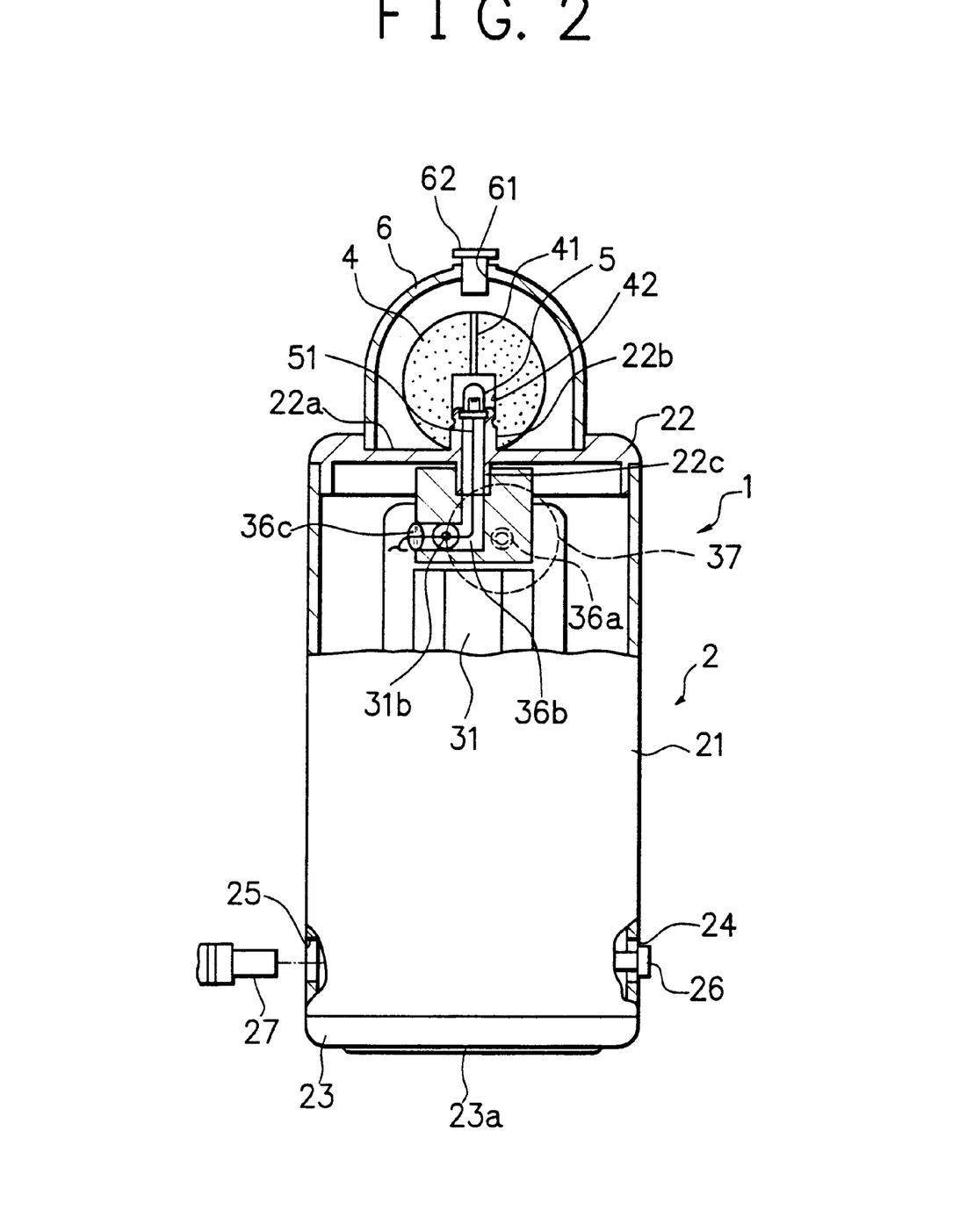
FIG. 2 is a partially cutaway side elevation of the diffuser made pursuant to the first embodiment of the present invention.
Figure 3:
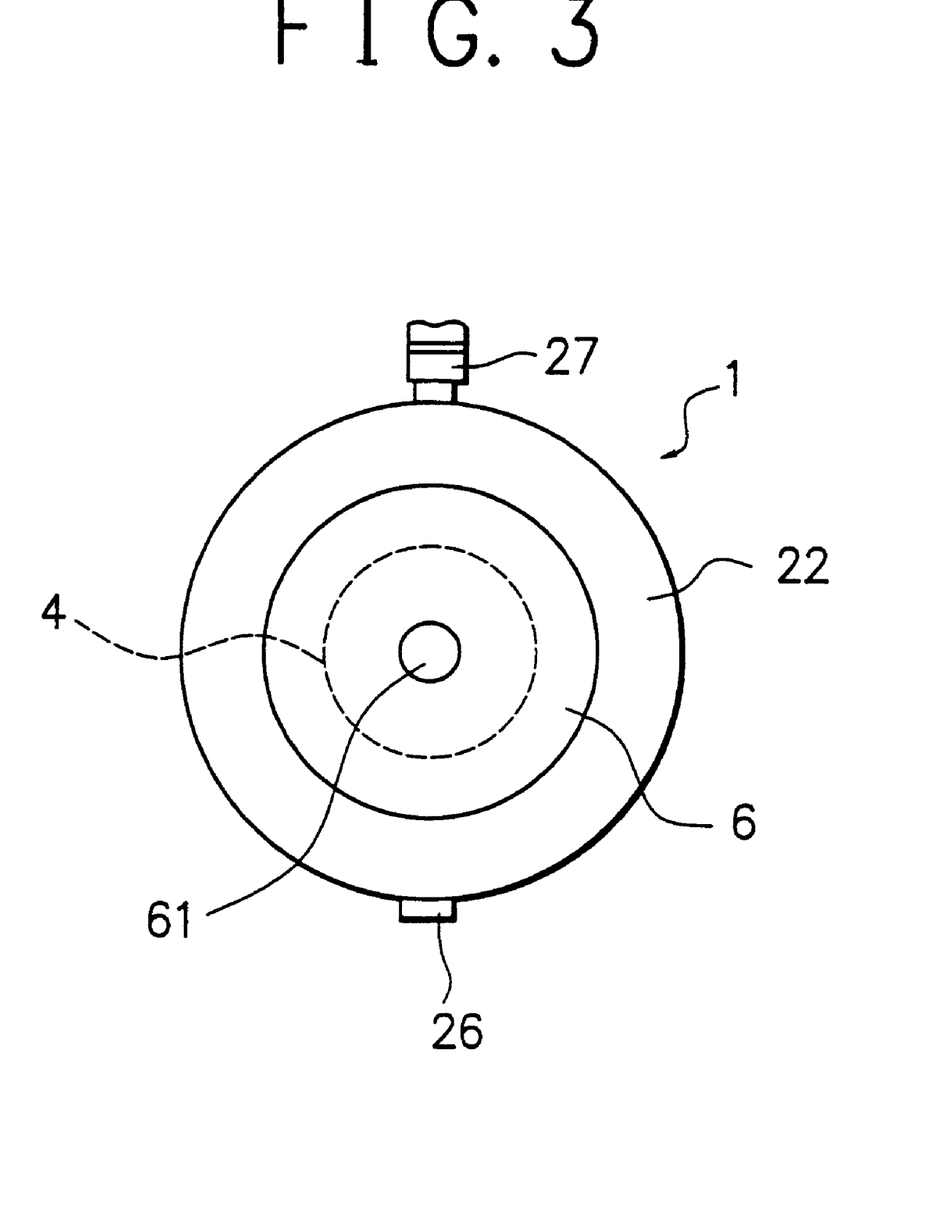
FIG. 3 is a plan view of the diffuser made pursuant to the first embodiment of the present invention.

The diffuser 1 has a casing 2 mounted with an actuator within it. The casing 2 has a casing body 21 which has an opening at each of its top and bottom and whose top and bottom are blocked up with lids 22 and 23. As shown in FIG. 2, two blowholes 24 and 25 are provided in the lower part of the casing body 21 in order to intake the air. One blowhole 24 also functions as an operating hole of a power switch 26 for actuating devices, and the other blowhole 25 functions as a connecting hole of a plug 27 for connecting to an external power supply. The casing body 21 has a diameter of 60 mm which is almost the same size as that of a 250 ml can for drinks (canned juice, canned coffee, etc.), therefore the diffuser 1 can be installed inside a car and held in a can holder for drinks (not illustrated herein).

Figure 1:
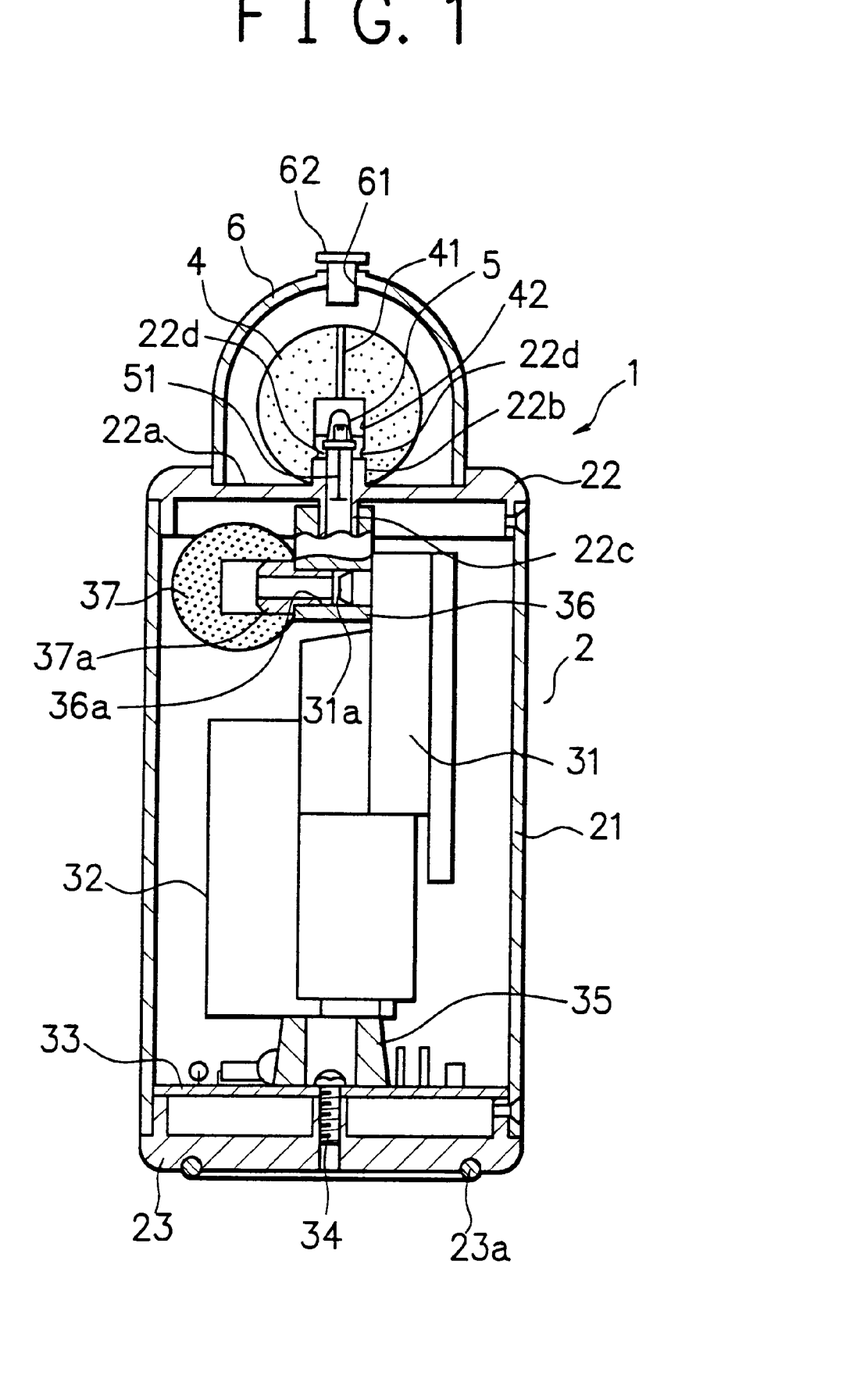
FIG. 1 is an elevational view in section of a diffuser made pursuant to the first embodiment of the present invention.

The casing 2 having the above makeup is mounted with an air feed pump 31, a battery 32, and a control substrate 33 for controling actuation of the air feed pump 31, etc. as well as controling electricity of a power supply. The control substrate 33 is connected to the lower lid 23 with a screw 34. The air feed pump 31 and the battery 32 are supported on the control substrate 33 via a vibration insulating support saddle 35. The lower surface of the lower lid 23 has a vibration insulating and non-slip rubber ring 23a embedded in it.

As shown in FIG. 1, a suction opening 31a of the air feed pump 31 is press-fitted in a suction passage 36a of a manifold 36. In the suction passage 36a a filter socket 37a of an air filter 37 is press-fitted. This allows the air in the casing 2 to be sucked into the air feed pump 31 through the air filter 37.

As shown in FIG. 2, a discharge opening 31b of the air feed pump 31 is press-fitted in a discharge passage 36b of the manifold 36. The upper lid 22 has a circular concave portion 22a formed on its upper surface which is a sump portion for liquid aromatic matter 71 discussed later. Further the upper lid 22 has cylindrical projections 22b and 22c, which are connected to each other through the lid 22, formed on the upper and lower surfaces of its central portion. On the upper projection 22b a spherical diffusing member 4 is removably press-fitted. In the lower projection 22c the discharge passage 36b of the manifold 36 is press-fitted. The upper part of the upper projection 22b has a slit 22d formed on it, as shown in FIG. 2, and the air flowing within the upper projection 22b flows into the diffusing member 4 through the slit 22d.

The upper part of the upper projection 22b has a light-emitting device, for example an incandescent lamp 5, equipped on it. The light emission of the incandescent lamp 5 allows the diffusing member 4 to be heated to about 40° C., in addition, the light leaks outside through the pores of the diffusing member 4. As shown in FIG. 2, a lead wire 51 of the incandescent lamp 5 is extended outside the manifold 36 through the lower projection 22c and the discharge passage 36b and is connected to the control substrate 33. In the portion outside the manifold 36 to which lead wire 51 is extended, that is, in the end portion of the discharge passage 36b, sealing material 36c is embedded so as to prevent the air from leaking out.

The above diffusing member 4 is made of porous member (polyethylene member) whose pores have a diameter of about 30 μm, so that the air fed into the diffusing member 4 is blown out through the pores. The diffusing member 4 has a slender hole 41 which vertically penetrates it. Since the slender hole 41 has a diameter of about 0.5 mm to 0.8 mm, air resistance there is small compared to that of the pores in the diffusing member 4. Further, the diffusing member 4 has a fitting hole (i.e., cavity) 42 formed in it so that it can be fitted on the upper projection 22b, and the slender hole 41 is connected to the fitting hole 42. The aforementioned air filter 37 is also made up of the same porous member as used for the diffusing member 4.

In the upper part of the upper lid 22 a transparent cap 6 is removably fitted to cover the diffusing member 4 and the concave portion 22a. The cap 6 is shaped like an inverted cup and a blowout hole 61 provided in the center of its top is sealed up with a removable stopper 62.

Figure 4:
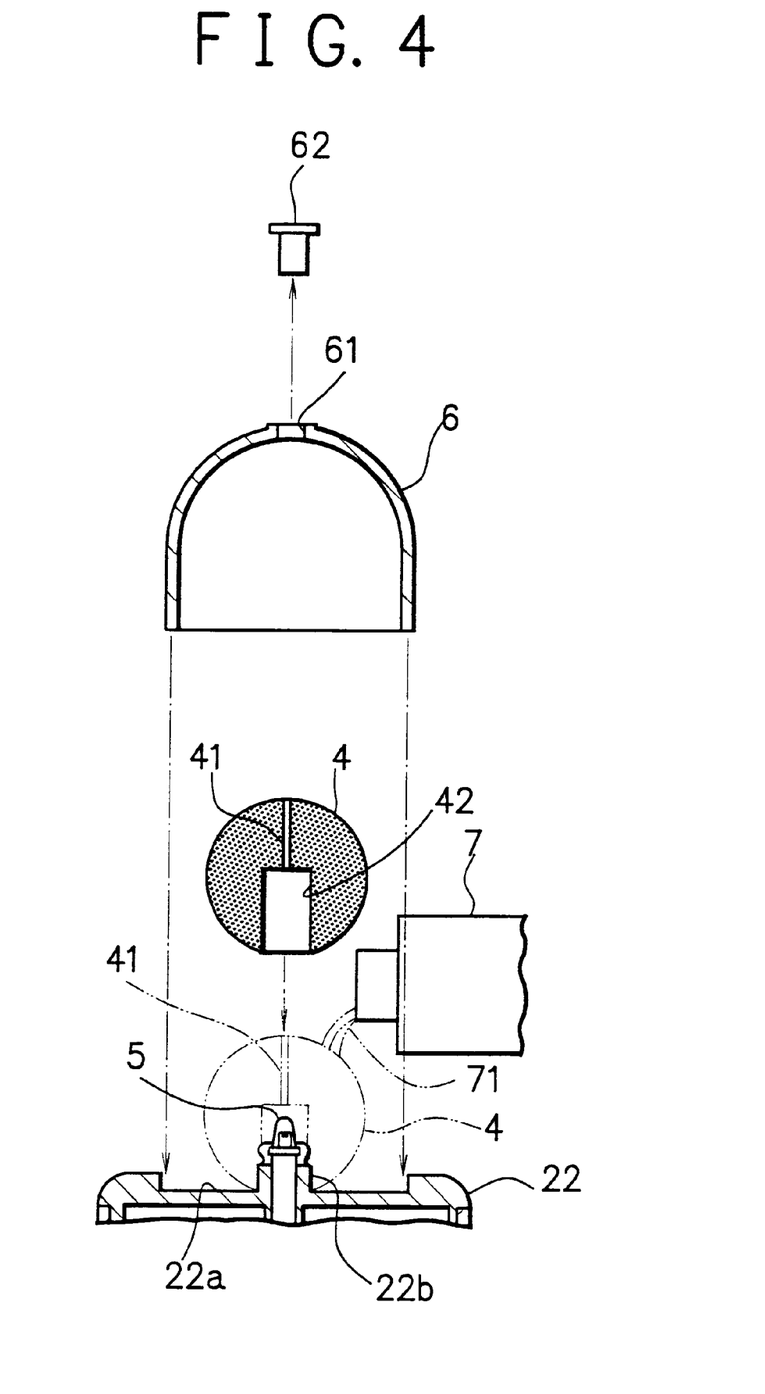
FIG. 4 is a view illustrating a diffusing member and a cap assembled into a diffuser made pursuant to the first embodiment of the present invention.

Now the use of the diffuser 1 made pursuant to the first embodiment of the present invention will be described with reference to FIG. 4. FIG. 4 illustrates one example of the diffuser 1 whose upper lid 22 is not equipped with the cap 6 and the diffusing member 4. In this diffuser 1, the diffusing member 4 is press-fitted on the upper projection 22b so that the incandescent lamp 5 can be housed in the fitting hole 42. Then the cap of a bottle 7 containing liquid aromatic matter (aromatic oil) 71 is opened, and the aromatic matter 71 will be dropped to the diffusing member 4 so as to be impregnated into the diffusing member 4. Alternatively, the aromatic matter 71 may be poured into the concave portion 22a of the upper lid 22 so as to be impregnated into the diffusing member 4. The aromatic matter 71 is not limited to be aromatic oil (essential oil containing extract of peppermint, rosemary, etc.), any aromatic matter can be applicable as far as it is liquid. After the above impregnating operation, the cap 6 with its stopper 62 removed is put on the upper lid 22.

After that, the diffuser 1 is placed in a room for which aromatization is intended, for example in a living room of a house, in a car, etc., and the power switch 26 is turned on. Here, when the diffuser 1 is connected to an external power supply through plug 27, electric power is supplied to each of the devices 5 and 31. On the other hand, when the diffuser 1 is not connected to an external power supply, electric power is supplied to each of the devices 5 and 31 from the battery 32. The supply of electric power allows the air feed pump 31 to be actuated and the incandescent lamp 5 to emit light.

The actuated air feed pump 31 allows the air surrounding the diffuser 1 to flow into the casing 2 through blowholes 24 and 25. The air flowed into the casing 2 first passes through the air filter 37 so that its dust will be removed, then through the filter socket 37a and through the suction passage 36a in order to be sucked into the air feed pump 31. The air sucked into the air feed pump 31 is then compressed in the air feed pump 31 to be blown out into the discharge passage 36b.

Figure 5:
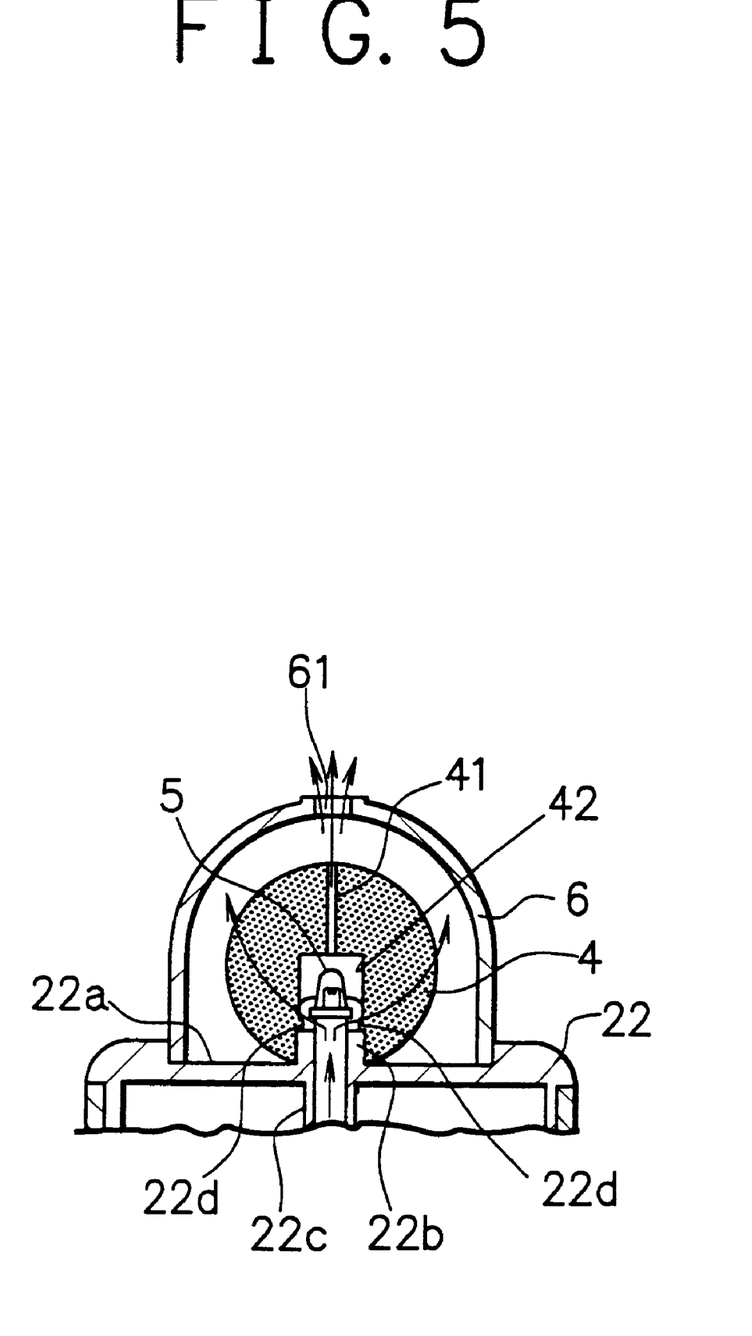
FIG. 5 is a sectional view illustrating a flow of the air passing through the diffuser made pursuant to the first embodiment of the present invention.

As shown in FIG. 5 with arrows, the air blown out into the discharge passage 36b flows into the diffusing member 4 through each of the projections 22b, 22c and the slit 22d. At this point, since the diffusing member 4 has been heated by the light emitted from the incandescent lamp 5, the aromatic matter 71 impregnated into the diffusing member 4 is subjected to or very susceptible to vaporization. Thus the incandescent lamp 5 functions to accelerate vaporization of, and moreover, diffusion of the aromatic matter 71. Further the air feed pump 31 functions to forcibly feed the air into the diffusing member 4, vaporize the aromatic matter 71, and moreover forcibly diffuse the vaporized aromatic matter 71.

Thus, the incandescent lamp 5 and the air feed pump 31 are formed as a device accelerating diffusion of the aromatic matter 71, that is a diffusion accelerator. The function of the diffusion accelerator allows a large quantity of aromatic matter 71 to get mixed in the air flowing into the diffusing member 4, the air with the aromatic matter 71 is blown out toward the cap 6 through the pores and slender hole 41 of the diffusing member 4. The air mixture blown out toward the cap 6 is further blown out outside of the diffuser 1 through the blowout hole 61 to be diffused over the whole room.

When the actuation of each of the devices 5 and 31 is subjected to timer-control, it may be controlled, for example, in such a manner that aromatizing operation is suspended about 20 minutes after the beginning of the aromatization.

When the diffuser 1 is not in use, the power switch 26 is turned off and the blowout hole 61 of the cap 6 is sealed up with the stopper 62, as shown in FIGS. 1 and 2.

According to the first embodiment of the present invention, the aromatic matter 71 impregnated into the diffusing member 4 is heated by the incandescent lamp 5 and, in addition, forcibly fed to the air in the room or the like by the air feed pump 31, therefore the whole room may be aromatized in a short time.

Further, since the diffusing member 4 has a slender hole 41, the liquid aromatic matter 71 impregnated into the diffusing member 4 is forcibly blown out in the spray state by the air passing through the slender hole 41. Thus the aromatic matter 71 does not remain in the diffusing member 4, and it does not clog up the diffusing member 4. Even if the diffusing member 4 is clogged up with the solidified aromatic matter 71 in its pores, the slender hole 41 having a larger cross-sectional area of flow allows the aromatic matter 71 to be fed to the air in the room or the like.

Further, the diffuser 1 made pursuant to the first embodiment of the present invention functions as an interior decoration at night, for the light of the incandescent lamp 5 leaks out through the pores and slender hole 41 of the diffusing member 4 and accordingly the whole diffusing member 4 emits light.

Still further, the portion sucking the air is equipped with the air filter 37 made up of the porous member while the portion discharging the air is equipped with the diffusing member 4 made up of a porous member; therefore an actuating noise made by the air feed pump 31 is attenuated in each of the members 37 and 4. Thus both members 37 and 4 function as silencers.

Still further, when using another kind of aromatic matter 71, nothing is needed but to replace the diffusing member 4 with a new one and drop another kind of aromatic matter 71 into it. Thus various kinds of aroma may be easily obtained.

Further, since the diffusing member 4 is made up of the porous member, of the aromatic matter 71 impregnated into the diffusing member 4 only some which exists on the surface of the diffusing member 4 comes into contact with the surrounding air. That is, dust and bacteria suspended in the surrounding air do not adhere to the whole aromatic matter 71; accordingly the deterioration of the aromatic matter 71 may be retarded.

In this embodiment aromatization of the air in the room is performed using liquid aromatic matter 71, however deodorization of the air in the room may also be performed using liquid deodorant matter instead of the aromatic matter. Further insecticide in the room may also be performed using liquid insecticidal matter instead of the aromatic matter. Still further humidification of the air in the room may also be performed using water only instead of the aromatic matter. Further a rubber tube, which is not illustrated in the figures, may be connected to the blowout hole 61 of the cap 6 so that aromatic matter can be introduced into a sauna, a bathroom of an inn with a hot spring, or a bathroom of an ordinary family. The stopper 62 is fitted into the blowout hole 61 of the cap 6 for the time when the diffuser is not in use, however it is not always necessary. Further, an ultraviolet lamp, which is not illustrated in the figures, may be equipped instead of the incandescent lamp 5 equipped in the diffusing ember 4. Ultraviolet rays emitted from the ultraviolet lamp prevents bacterial propagation in the diffusing member 4.

FIGS. 6 to 9 illustrate a diffuser made pursuant to the second embodiment of the present invention. Here the diffuser will be described using the same numerical symbols as the aforementioned first embodiment for the constituent parts common to both embodiments.

Figure 6:
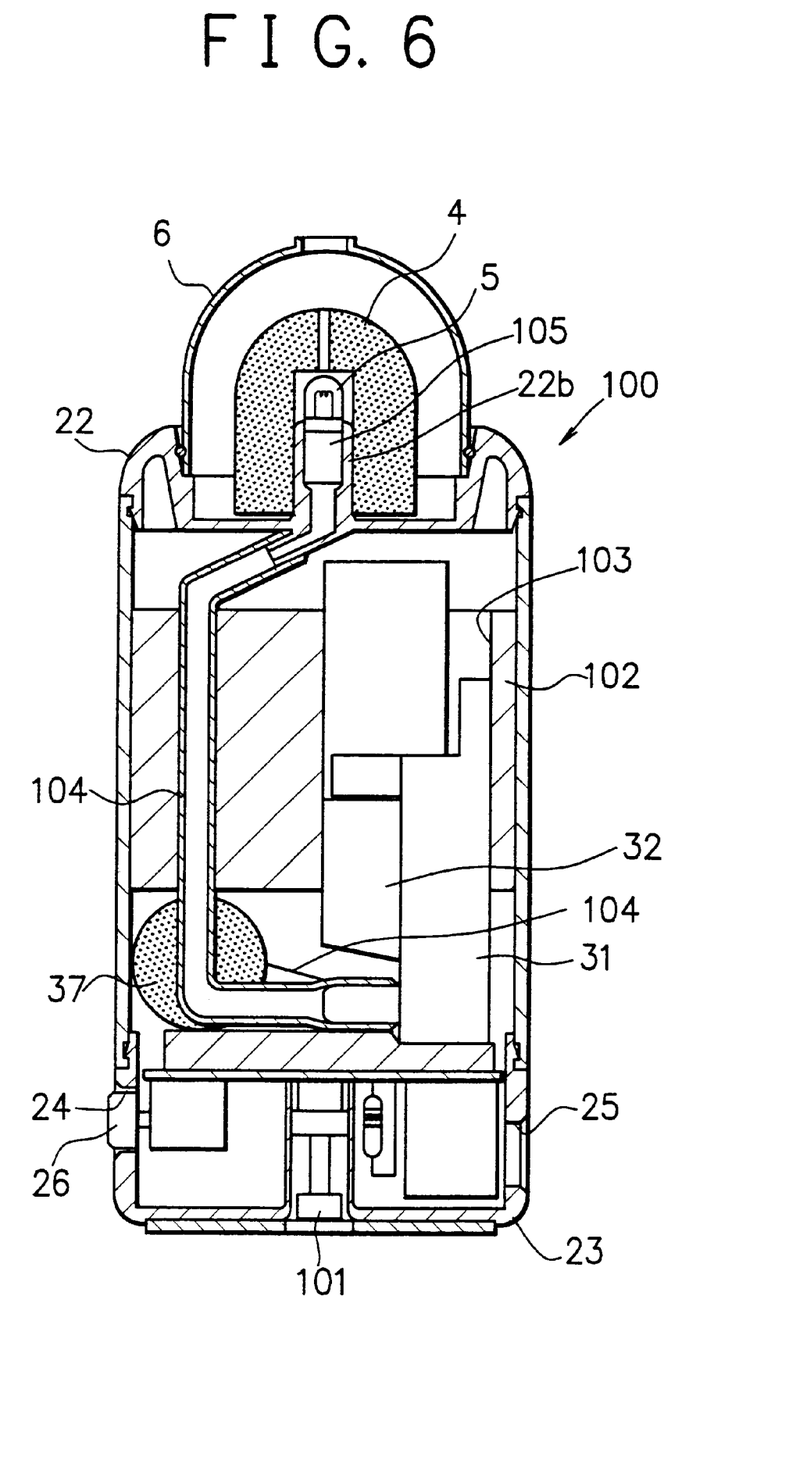
FIG. 6 is an elevational view in section of a diffuser made pursuant to the second embodiment of the present invention.
Figure 7:
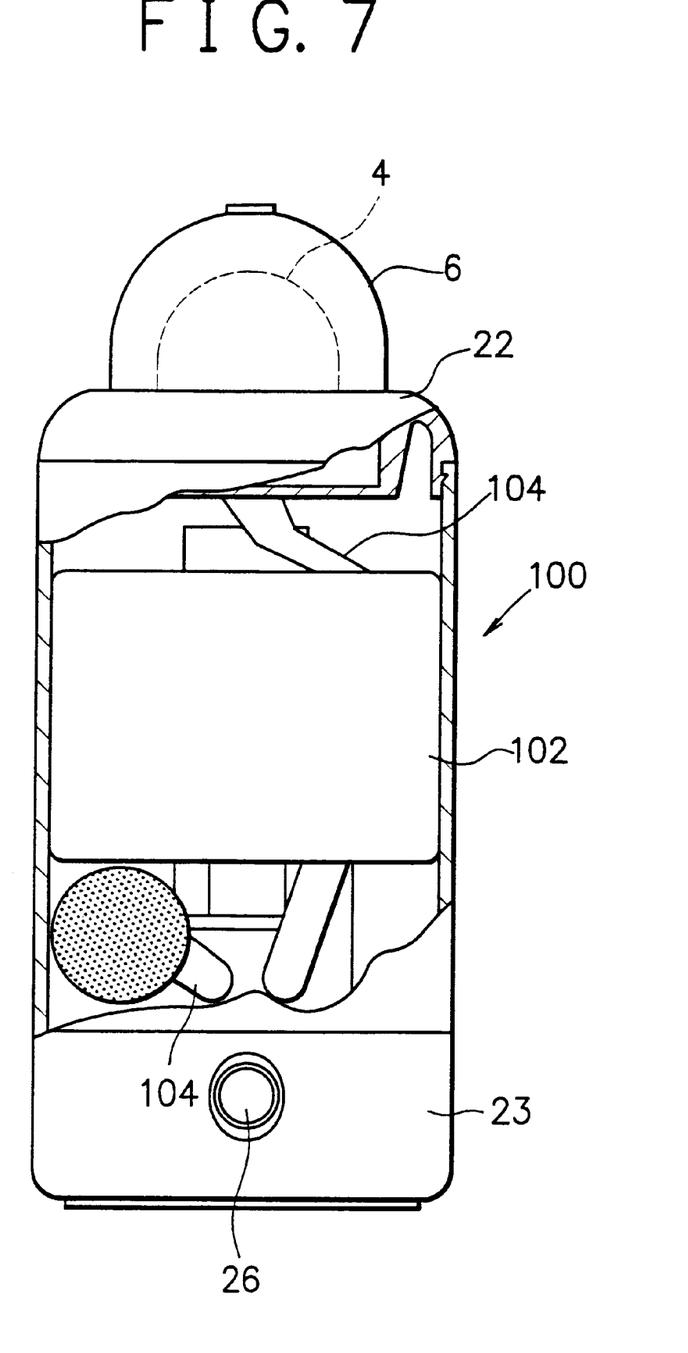
FIG. 7 is a partially cutaway side elevation of the diffuser made pursuant to the second embodiment of the present invention.

The main difference in structure between diffuser 100 according to the second embodiment of the present invention and diffuser 1 according to the first embodiment of the present invention will be described below. The diffuser 100 according to the second embodiment has a changeover switch 101 in addition to a power switch 26. As shown in FIG. 6, the changeover switch 101 is arranged so as to penetrate the lower lid 23. With the changeover switch 101, the choice can be made of the operation of turning on the electricity of both the air feed pump 31 and the incandescent lamp 5 or the operation of turning on the electricity only of the incandescent lamp 5 (the electricity of the air feed pump 31 is turned off).

In the second embodiment, a holding block 102 made of foam polyurethane rubber or the like is used as measures for holding a battery 32 as well as an air feed pump 31. The holding block 102 has space 103 running through it vertically, and the battery 32 and the air feed pump 31 are press-fitted into the space 103. The holding block 102 in which each of the devices 31 and 32 is press-fitted is press-fitted in casing body 21.

In the aforementioned first embodiment, the air filter 37 and the suction opening 31a of the air feed pump 31 are connected to each other in the manifold 36 and the lower projection 22c and the discharge opening 31b of the air feed pump 31 are also connected to each other in the manifold 36. On the other hand, in the second embodiment, a flexible pipe 104 made of silicone rubber or the like is used as a connecting member for connecting those parts.

Figure 8:
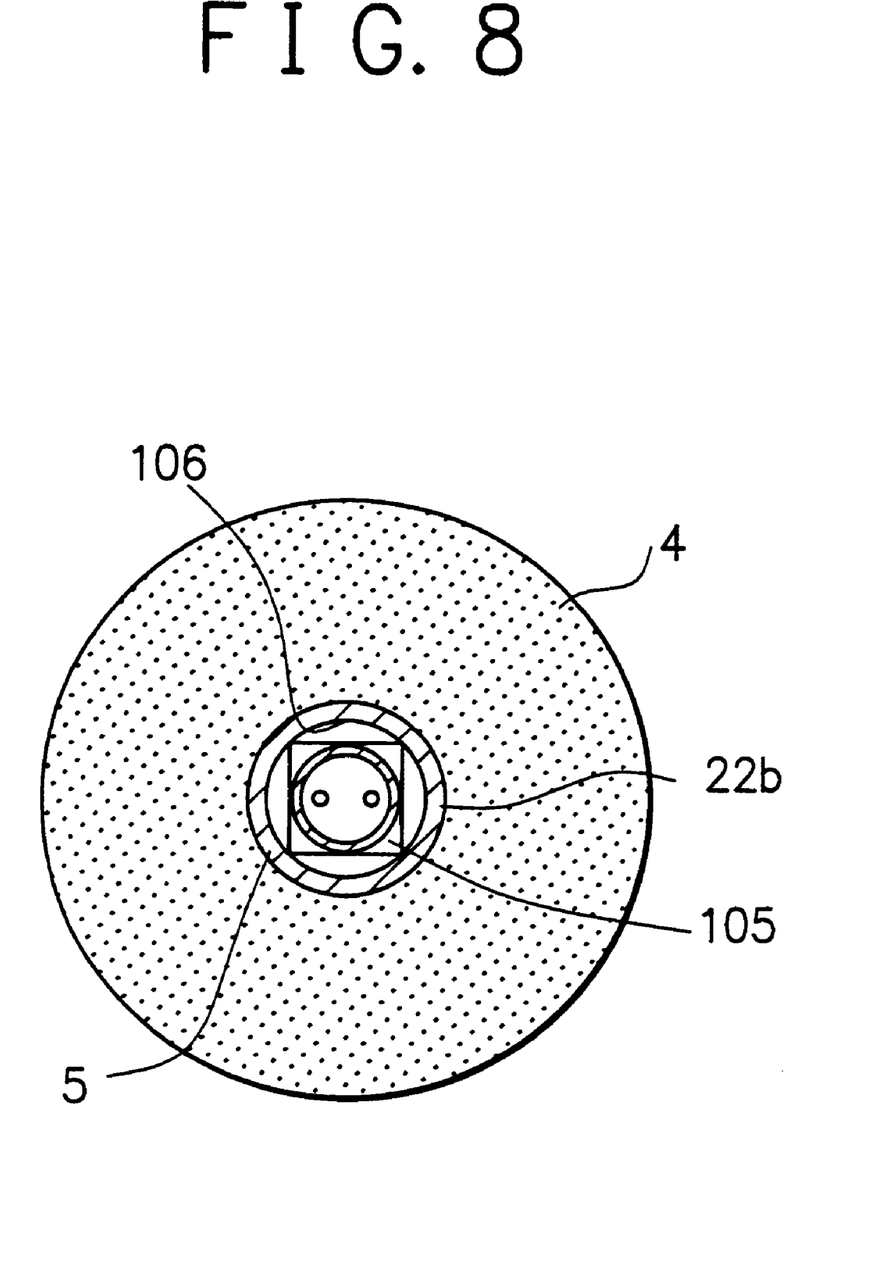
FIG. 8 is a sectional view illustrating a state of an incandescent lamp attached to the diffuser made pursuant to the second embodiment of the present invention.

As shown in FIGS. 6 and 8, a square connector 105 is equipped inside the cylindrical upper projection 22b, and terminals of the incandescent lamp 5 are inserted into the connector 105. Between the connector 105 and the internal surface of the upper projection 22b there is clearance 106 through which the air flows.

Figure 9:
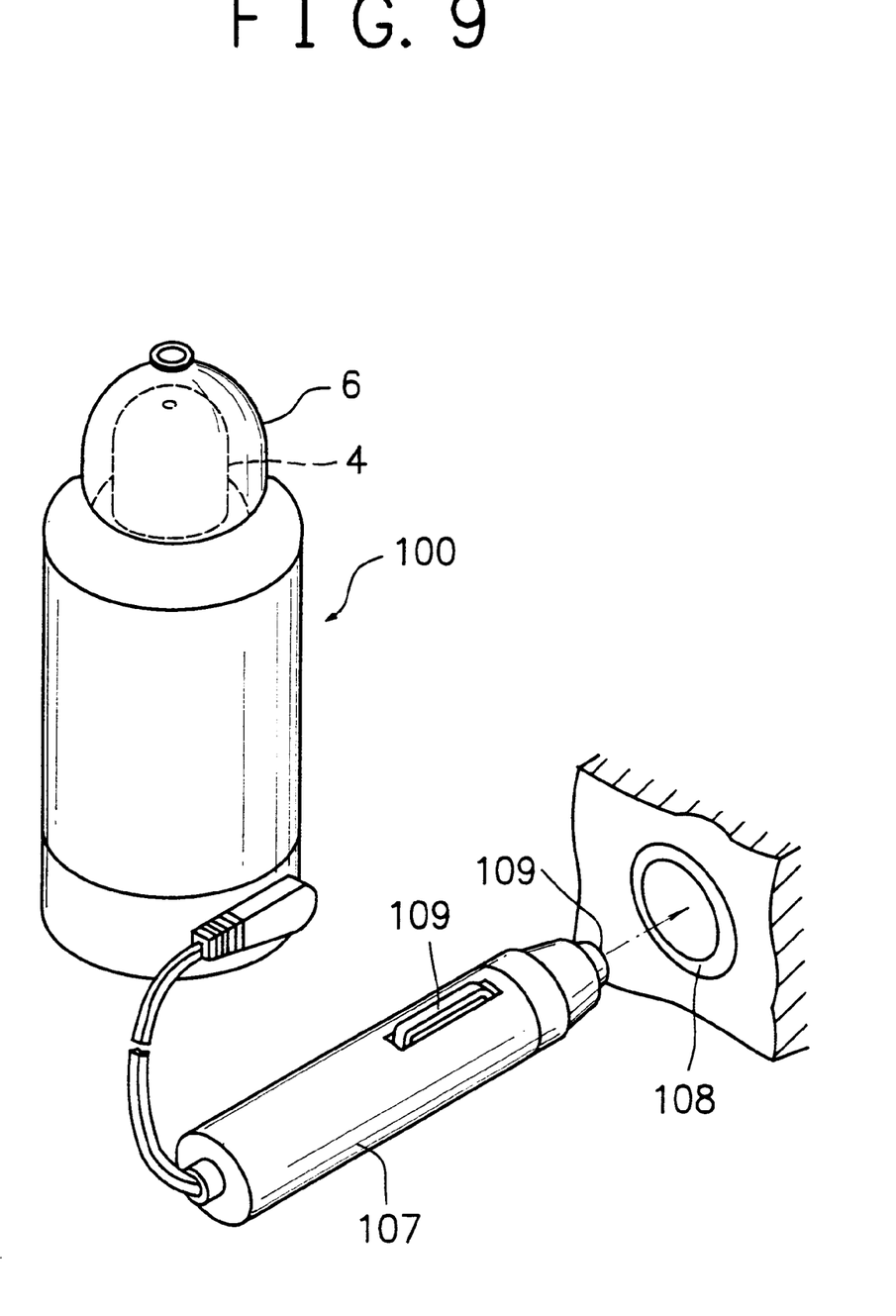
FIG. 9 is a perspective view illustrating a state of an electric connection of the diffuser made pursuant to the second embodiment of the present invention.

As shown in FIG. 9, a jack 107 is used which is connected to an external power supply. The jack 107 has the same overall size as a cigarette lighter of cars and has terminals 109 at its tip as well as on its circumference sidewall of the tip side. Such makeup of the jack 107 allows the diffuser 100 to be removably attached to a socket 108 for a cigarette lighter.

According to the second embodiment of the present invention, when the operation is chosen to turn on the electricity of both the air feed pump 31 and the incandescent lamp 5 by using the changeover switch 101, a large quantity of the aromatic matter 71 impregnated into the diffusing member 4 is diffused over the whole room of the car in a short time. Once aromatization of the air over the whole room of the car is completed, if the operation is chosen to turn on the electricity only of the incandescent lamp 5 by using the changeover switch 101, aromatization in the car may be kept on using a small quantity of the aromatic matter.

When using the diffuser 100, nothing is needed but to insert the jack 107 into the socket 108; thus aromatization in the car may be easily carried out.

The other makeup of the second embodiment of the present invention is almost the same as the aforementioned first embodiment.

Figure 10:
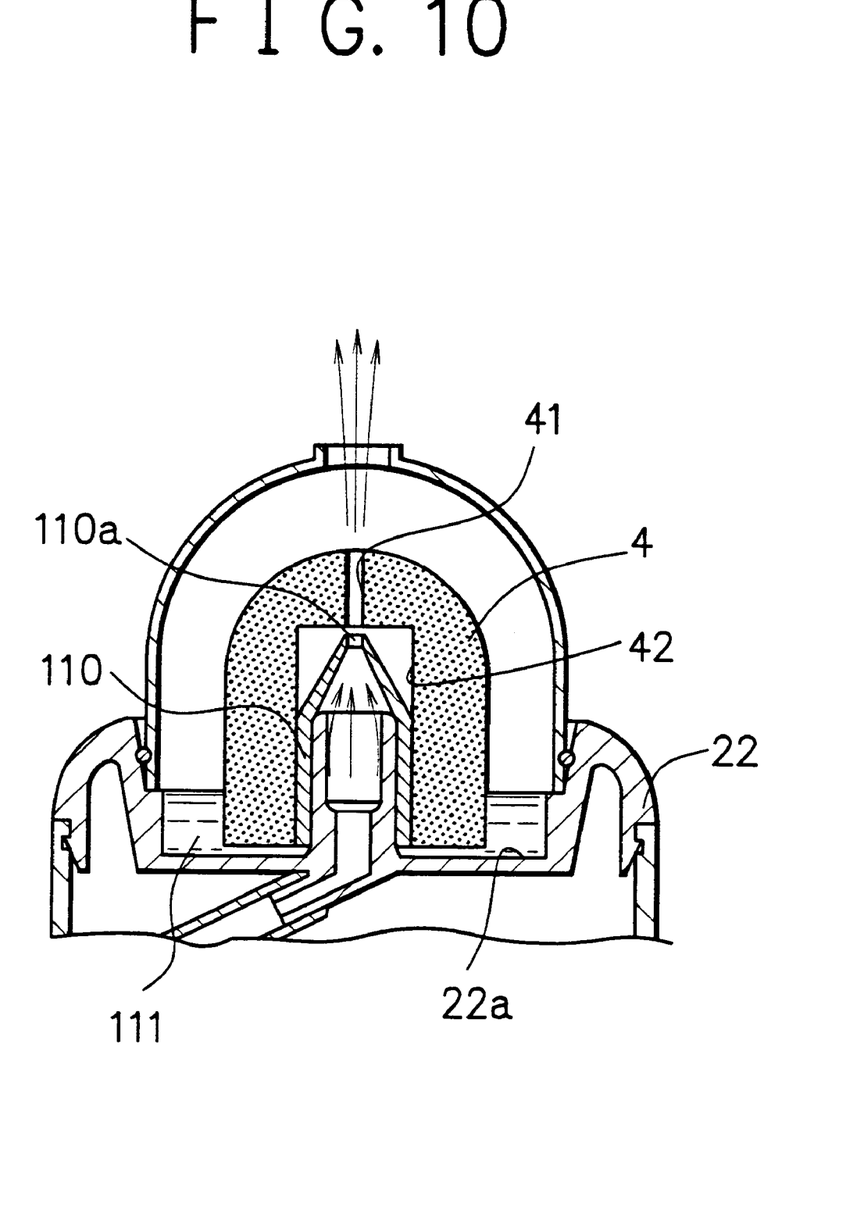
FIG. 10 is a main portion sectional view of a modified example of the diffuser made pursuant to the second embodiment of the present invention.

FIG. 10 illustrates one example of the modified diffuser made pursuant to the second embodiment of the present invention. In the modified example, a roughly conical nozzle 110 is equipped between the fitting hole 42 of the diffusing member 4 and the upper projection 22b. The nozzle 110 is provided with a small bore 110a at its tip so that the air may be blown out toward the slender hole 41 of the diffusing member 4 through the small bore 110a.

When humidifying the air in the room using the above diffuser, water 111 is previously put into the concave portion 22a of the upper lid 22. When the diffusing member 4 is soaked in water 111, water 111 permeates the whole diffusing member 4 due to capillary phenomenon. After that, when actuating the air feed pump 31, the air flows inside the nozzle 110 and then blown out outside through the small bore 110a and the slender hole 41, as shown with solid arrows. Here, since the flow rate of the air passing through the slender hole 41 is high and the pressure inside the slender hole 41 becomes negative, the water impregnated into the diffusing member 4 is attracted toward the slender hole 41 and blown out outside in the mist state. Humidification in the room is thus performed.

With the modified diffuser, since most of the air fed from the air feed pump 31 passes through the nozzle 110 and the slender hole 41, a large quantity of air in the mist state, which is suitable for humidification, is fed to a room.

When changing the space between the small bore 110a of the nozzle 110 and the slender hole 41, for example when widening the space, the flow rate of the air flowing through the slender hole 41 becomes slower, so that the quantity of water attracted toward the slender hole 41 becomes smaller. On the other hand, when narrowing the space, the flow rate of the air flowing through the slender hole 41 becomes higher, so that the quantity of water attracted toward the slender hole 41 becomes larger. Accordingly, the humidifying amount per unit time may be regulated by adjusting the above space.

Figure 11:
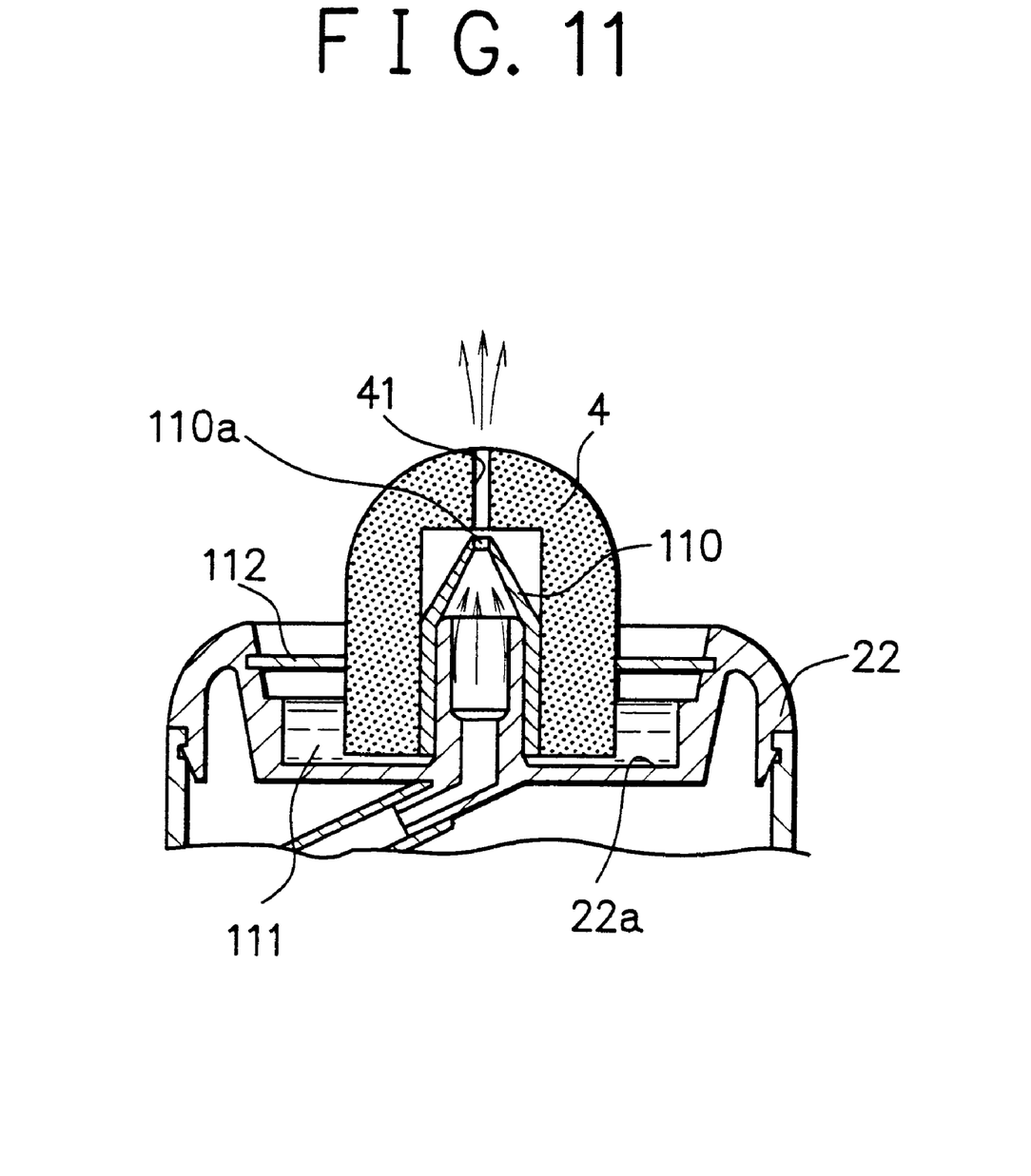
FIG. 11 is a main portion sectional view of another modified example of the diffuser made pursuant to the second embodiment of the present invention.

FIG. 11 illustrates another example of the modified diffuser which is an improvement of the aforementioned modified diffuser. The modified diffuser made by improving the above modified diffuser is provided with a rubber covering board 112 removably fitted in the internal circumference of the concave portion 22a of the upper lid 22, wherein the diffusing member 4 is fitted in the center of the covering board 112. The covering board 112 is fitted in and on the concave portion 22a and the diffusing member 4 airtightly.

With the modified diffuser, when the diffuser is overturned by mistake, water 111 stored in the concave portion 22a is never leaked out.

In each of the above modified examples, the incandescent lamp 5 and the connector 105 are removed from the upper projection 22b, however the incandescent lamp 5 and the connector 105 may be arranged in the upper projection 22b. When the incandescent lamp 5 and the connector 105 are arranged in the upper projection 22b, nozzle 110 is made of a transparent member so that the light of the incandescent lamp 5 can irradiate the diffusing member 4. Further in the above modified examples, although water 111 for humidification is stored in the concave portion 22a of the upper lid 22, in case of shortage of the water, a water feed device which is not illustrated in the figure may be installed so as to feed water into the concave portion 22a. Further a water tank, which is not illustrated in the figure, may be arranged around the diffuser with one portion of the diffusing member 4 extended to the water tank to be soaked in water, so that water will be drawn from the water tank due to capillary phenomenon. Still further, a humidity detector which detects humidity in the room of a car may be installed so that the humidifying amount of the diffuser can be regulated based on the detected humidity value obtained from the humidity detector.

Figure 12:
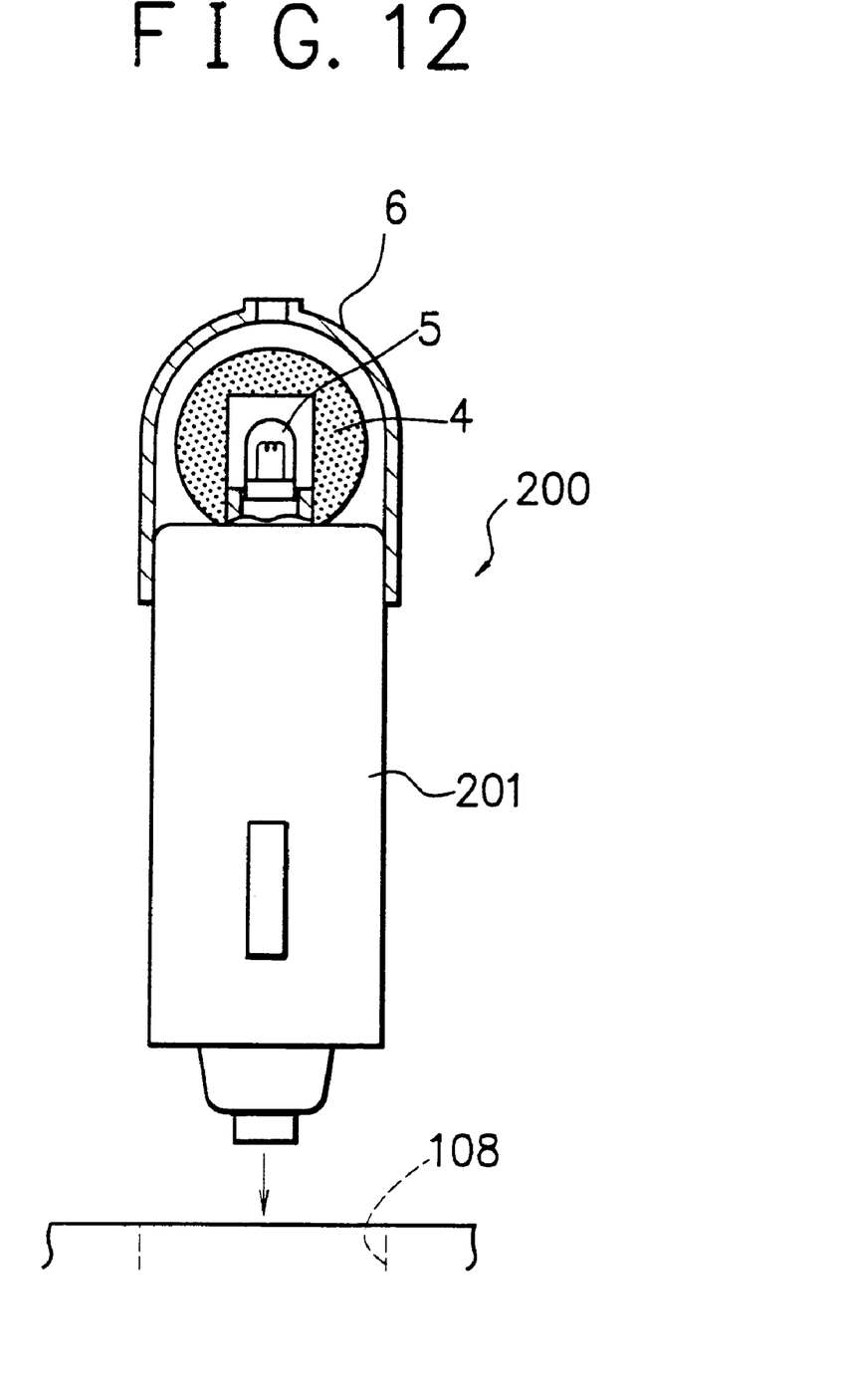
FIG. 12 is a partially cutaway side elevation of a diffuser made pursuant to the third embodiment of the present invention.

FIG. 12 illustrates a diffuser made pursuant to the third embodiment of the present invention. The diffuser 200 made pursuant to the third embodiment is provided with a jack 201 having the same makeup as that of the aforementioned second embodiment. The jack 201 has an incandescent lamp 5 and a diffusing member 4 attached to it, wherein the diffusing member 4 is removably covered with a cap 6. The jack 201, unlike those of the first and second embodiments, is not mounted with an air feed pump and so on.

With the diffuser made pursuant to the third embodiment, nothing is needed but to directly insert the jack 201 into a socket 108 for a cigarette lighter, aromatization in a car is easily performed.

Figure 13:
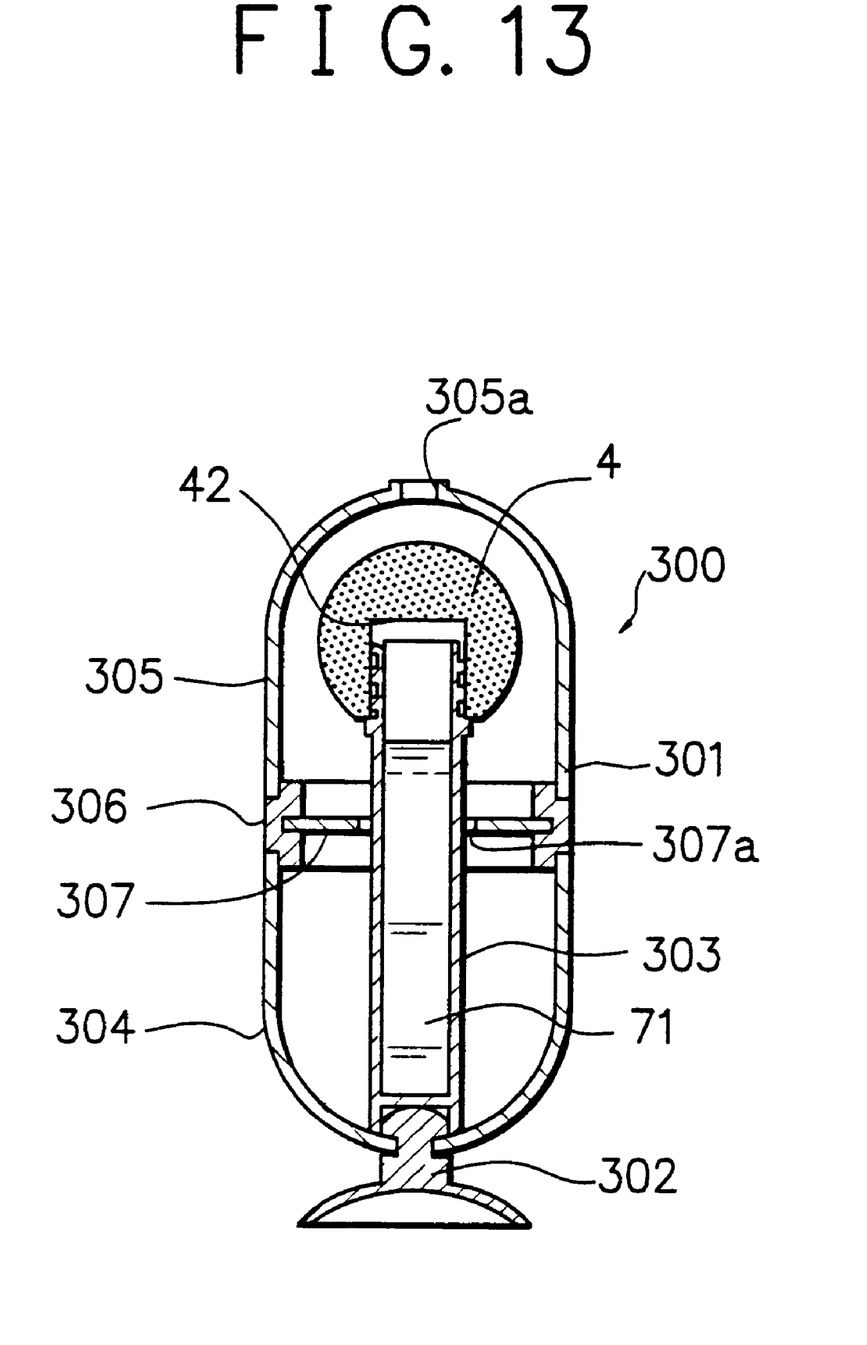
FIG. 13 is an elevational view in section of a diffuser made pursuant to the fourth embodiment of the present invention.
Figure 14:
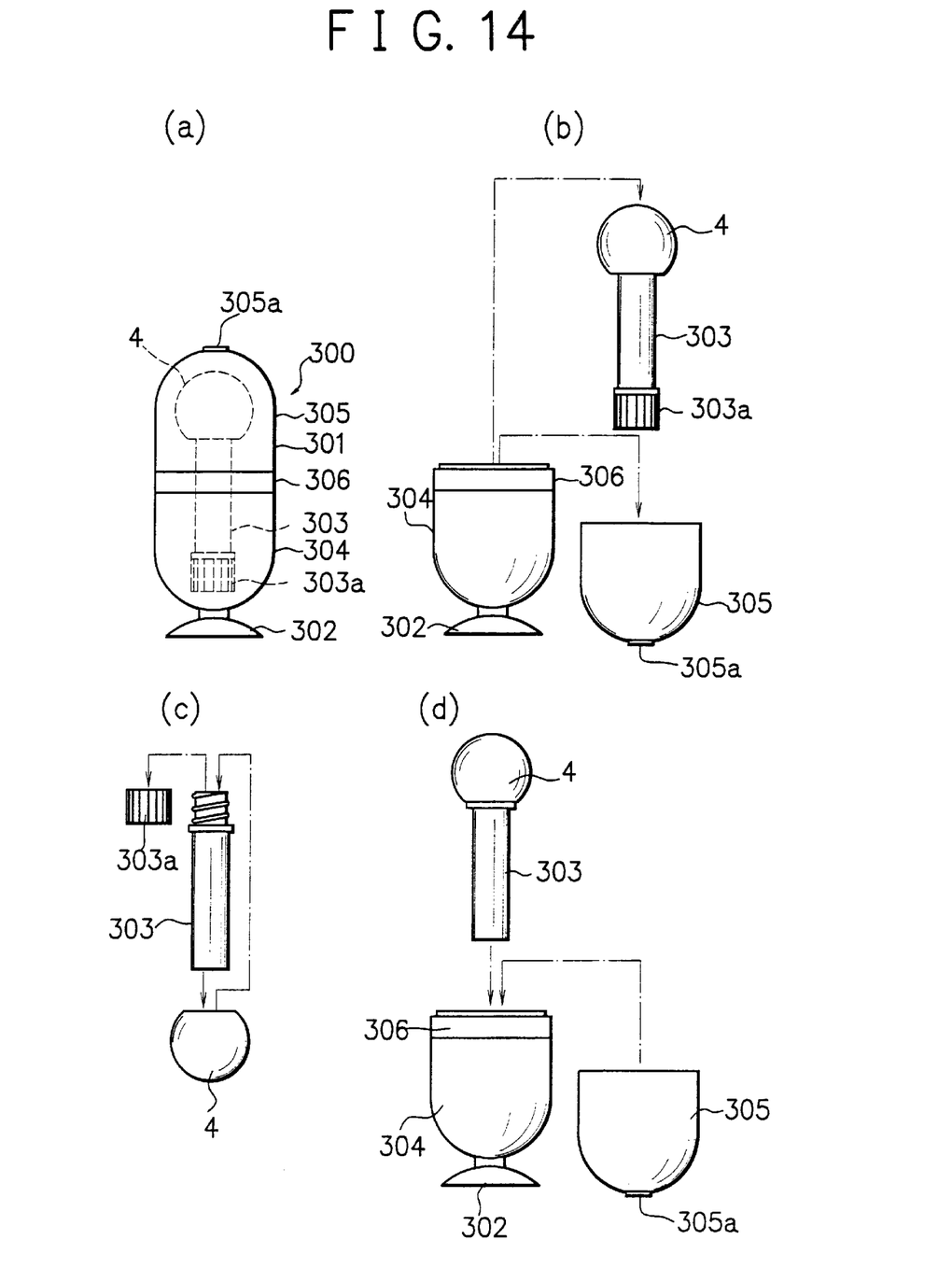
FIG. 14(a)–FIG. 14(d) illustrate the use of the diffuser made pursuant to the fourth embodiment of the present invention.

FIG. 13 and FIGS. 14(a), (b), (c) and (d) illustrate a diffuser made pursuant to the fourth embodiment of the present invention. The diffuser 300 is made up of a roughly oval casing 301, an adsorbent 302 for fixing the casing 301, a diffusing member 4 stored in the casing 301, and a cartridge 303 in which liquid aromatic matter 71 is stored.

The casing 301 has a storage space 304, whose section is U-shaped, as well as a cap space 305 and is formed with each of the portions 304 and 305 fitted on the top and bottom surfaces of an annular fitting board 306. The storage space 304 and the cap space 305 are made of a transparent member so that the diffusing member 4 and the cartridge 303 housed in the casing 301 can be seen through them. The cap 305 is removably attached to the fitting board 306, and removal of the cap 305 makes it possible to take out the diffusing member 4 and the cartridge 303 from the casing 301. The cap space 305 has a blowout hole 305a formed on its upper end so that the air in the casing 301 can be diffused outside through the blowout hole 305a. The storage space 304 has the adsorbent 302 attached on its lower end for fixing the diffuser so that the diffuser can be fixed on a front panel of a car, on a desk of one's room, etc. by the adsorbent 302.

Inside the fitting board 306 a holding board 307 is fitted which divides the inside space of the casing 301 into an upper and lower parts. In the center of the holding board 307 a penetrating hole 307a is provided so that the cartridge 303 penetrating the penetrating hole 307a will be held by the holding board 307 to have play.

The use of the diffuser 300 made pursuant to the fourth embodiment of the present invention will be described with reference to FIGS. 14(a), (b), (c) and (d). Before using the diffuser 300, the cartridge 303 and the diffusing member 4 are stored in the casing 301, as shown in FIG. 14(a). As shown in FIG. 14(b), first the cap space 305 is removed from the casing 301, then the cartridge 303 and the diffusing member 4 stored in the casing 301 are taken out. Here, the diffusing member 4 is stored in the casing 301 in state where it is fitted on the end of the cartridge 303. Then, as shown in FIG. 14(c), the diffusing member 4 is removed from the cartridge 303 and a lid 303a of the cartridge 303 is also removed. A fitting hole 42 of the diffusing member 4 is fitted to the opening of the cartridge 303, and the diffusing member 4 is fitted on the opening of the cartridge 303. After that, the cartridge 303 on which the diffusing member 4 is fitted is shaken vertically so that liquid aromatic matter 71 in the cartridge 303 will be impregnated into the diffusing member 4. Then, as shown in FIG. 14(d), the cartridge 303 is put into the storage space 304 of the casing 301 from its end so as to penetrate the penetrating hole 307a, as shown in FIG. 13. Finally, the cap space 305 is fitted on the fitting board 306, and the adsorbent 302 is adsorbed on a front panel of a car or the like. With the diffuser 300, aromatization in the room of a car is thus performed.

According to the fourth embodiment of the present invention, since the diffusing member 4 is made of a porous member, the deterioration of aromatic matter 71 may be retarded just like the aforementioned embodiments.

Further, since not only the diffusing member 4 but also the cartridge 303 storing the aromatic matter 71 are housed in the casing 301, the diffuser is conveniently used.

Needless to say, water, liquid deodorant matter or liquid insecticidal matter instead of the aromatic matter 71 may be stored in the cartridge 303. An incandescent lamp and a small-sized battery, which are not illustrated in the figures, may be embedded in the diffusing member 4 so that aromatic matter or the like will be vaporized by the heat generated from the incandescent lamp.

What is claimed is:

1. A diffuser comprising:
   a housing, a detachable porous diffusing member impregnated with a diffusable liquid, the diffusing member including a plurality of diffusing pores each having a diameter of approximately 30 µm, the diffusable liquid being selected from the group comprising water, liquid aromatic matter, liquid deodorant matter, and liquid insecticidal matter, an incadescent lamp housed within the diffusing member and being adapted and arranged to emit radiant energy to heat the diffusing member to a temperature of approximately 40° C., an air feed pump for feeding air into the diffusing member, the housing including a support structure for the diffusing member, the support structure and the diffusing member being arranged so the diffusing member is press fit on the support structure to enable the diffusing member to be detachable form the support structure, the support structure carrying the lamp and the diffusing member including a cavity, the lamp and the cavity being sized and arranged so all portions of the lamps periphery are within the cavity and spaced from the diffusing member while the diffusing member is press fit to the support structure.

2. The diffuser of claim 1 wherein the support structure has a projecting portion extending into the diffusing member to provide at least a portion of a press fit surface.

3. The diffuser of claim 2, wherein the diffusing member includes a cavity into which the projecting portion extends, an end of the projecting portion in the cavity carrying the lamp, the lamp and the cavity being sized and arranged so all portions of the lamp periphery are spaced from the diffusing member while the diffusing member is press fit to the support structure.

4. A diffuser comprising:

a housing, a detachable porous diffusing member impregnated with a diffusable liquid, the diffusing member including a plurality of diffusing pores each having a diameter of approximately 30 µm, the diffusable liquid being selected from the group comprising water, liquid aromatic matter, liquid deodorant matter, and liquid insecticidal matter, an incandescent lamp housed within the diffusing member and being adapted and arranged to emit radiant energy to heat the diffusing member to a temperature of approximately 40° C., an air feed pump for feeding air into the diffusing member, the housing including a support structure for the diffusing member, the support structure and the diffusing member being arranged so the diffusing member is press fit on the support structure to enable the diffusing member to be detachable form the support structure, the support structure having a projecting portion extending into the diffusing member to provide at least a portion of a press fit surface, the diffusing member including a cavity into which the projecting portion extends, an end of the projecting portion in the cavity carrying the lamp, the lamp and the cavity being sized and arranged so all portions of the lamp periphery are spaced from the diffusing member while the diffusing member is press fit to the support structure, the projecting portion including an air discharge outlet of the air feed pump, the air discharge outlet being in fluid communication with the cavity of the diffusing member.

5. The diffuser of claim 4, wherein the projecting portion includes an inner air passageway defining the air discharge outlet of the air feed pump, and a peripheral slot in fluid communication with the inner passageway and the cavity of the diffusing member.

* * * * *